(12) United States Patent
Yazicioglu et al.

(10) Patent No.: US 8,466,742 B2
(45) Date of Patent: Jun. 18, 2013

(54) LARGE TIME CONSTANT STEERING CIRCUIT AND INSTRUMENTATION AMPLIFIER IMPLEMENTING SAME

(75) Inventors: Refet Firat Yazicioglu, Leuven (BE); Patrick Merken, Montenaken (BE)

(73) Assignees: IMEC, Leuven (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 323 days.

(21) Appl. No.: 13/035,210

(22) Filed: Feb. 25, 2011

(65) Prior Publication Data

US 2011/0193623 A1 Aug. 11, 2011

Related U.S. Application Data

(62) Division of application No. 12/362,687, filed on Jan. 30, 2009, now Pat. No. 7,920,005.

(60) Provisional application No. 61/024,954, filed on Jan. 31, 2008.

(30) Foreign Application Priority Data

Jul. 14, 2008 (EP) .................................... 08160365

(51) Int. Cl.
 *H03F 3/68* (2006.01)
(52) U.S. Cl.
 USPC ............................ 330/103; 330/252; 330/276
(58) Field of Classification Search
 USPC ........................................ 330/103, 252, 276
 See application file for complete search history.

(56) References Cited

U.S. PATENT DOCUMENTS

| | | | | |
|---|---|---|---|---|
| 3,601,676 A | * | 8/1971 | Halfhill et al. | 318/592 |
| 3,646,420 A | * | 2/1972 | Halfhill et al. | 318/634 |
| 5,461,322 A | * | 10/1995 | Bey et al. | 324/706 |
| 5,793,241 A | | 8/1998 | Sanzo et al. | |
| 5,953,690 A | * | 9/1999 | Lemon et al. | 702/191 |
| 7,795,960 B2 | | 9/2010 | Lyden et al. | |
| 7,796,173 B2 | | 9/2010 | Lettvin | |

OTHER PUBLICATIONS

R F. Yazicioglu, P. Merken, R. Puers, and C. Van Hoof, "60_μW 60nV/pHz readout front-end for portable biopotential acquisition systems," IEEE J. Solid-State Circuits, vol. 42, No. 5, pp. 1100-1110, May 2007.
T. Denison, K. Consoer, W. Santa, T. Avestruz, J. Cooley, and A. Kelly, "A 2μW 100nV/√4Hz Chopper-Stabilized Instrumentation Amplifier for Chronic Measurement of Neural Field Potentials," IEEE J. Solid-State Circuits, vol. 42, No. 12, Dec. 2007.

(Continued)

*Primary Examiner* — Patricia Nguyen
(74) *Attorney, Agent, or Firm* — McDonnell Boehnen Hulbert & Berghoff LLP (57) ABSTRACT

The present invention relates to a large time constant steering circuit for slowly changing a voltage on a node between at least two discrete voltage levels. The present invention further relates to a slow steering current DAC comprising said large time constant steering circuit. The present invention further relates to an instrumentation amplifier device comprising a current balancing instrumentation amplifier for amplifying an input signal to an amplified output signal and a DC servo-loop for removing a DC-component from the input signal. The present invention further relates to an EEG acquisition ASIC comprising said instrumentation amplifier device.

7 Claims, 6 Drawing Sheets

OTHER PUBLICATIONS

R. R. Harrison and C. Cameron, "A Low-Power Low-Noise CMOS Amplifier for Neural Recording Applications," IEEE J. Solid-State Circuits, vol. 38, No. 6, Jun. 2003.

R. H. Olsson, M. N. Gulari, and K. D. Wise, "A Fully-Integrated Bandpass Amplifier for Extracellular Neural Recording," IEEE EMBS Conf. on Neural Eng., Italy, Mar. 2003.

* cited by examiner

LARGE TIME CONSTANT STEERING CIRCUIT AND INSTRUMENTATION AMPLIFIER IMPLEMENTING SAME

CROSS-REFERENCE TO RELATED APPLICATIONS

This application is a divisional of and claims priority to U.S. patent application Ser. No. 12/362,687 filed Jan. 30, 2009, which claims priority under 35 U.S.C. §119(e) to U.S. Provisional Patent Application Ser. No. 61/024,954, filed on Jan. 31, 2008 and under 35 U.S.C. §119(b) to European Patent Application EP 08160365.6, filed on Jul. 14, 2008, the full disclosures of which are incorporated herein by reference.

FIELD

The present invention relates to a large time constant steering circuit for slowly changing a voltage on a node between at least two discrete voltage levels. The present invention further relates to a slow steering current DAC comprising said large time constant steering circuit.

BACKGROUND

In order to remove the DC component of a signal or to eliminate DC offset, most integrated circuits rely on high-pass filters. Most commonly used examples of a high-pass filter are DC level shifters, DC blocking capacitors, and DC servo-loops.

Recently, there is much interest to develop instrumentation amplifiers with low-power dissipation, low-noise, high common mode rejection, and large input impedance for example towards the field of ambulatory biomedical signal monitoring. The large DC component of the biomedical signals necessitates the implementation of high-pass filter characteristics to the instrumentation amplifier.

These requirements lead to the usage of chopper-stabilized instrumentation amplifiers with high-pass filter characteristics. The most power efficient way of implementing high-pass filter characteristics to the chopper stabilized amplifiers is to use DC servo-loops [1], [2]. The DC servo-loop senses the DC level of the output and subtracts it from the input of the amplifier.

The previous implementations of the chopper stabilized amplifiers incorporating a DC servo-loop for implementing high-pass filter characteristics either subtract voltage, [2], or current, [1], from the input signal before it is amplified by the instrumentation amplifier. However, the prior technique results in large power dissipation due to the fact that the DC servo-loop must be capable of supplying wide range of current output, and the later reduces the input impedance of the amplifier.

In an attempt to reduce the power dissipation of a DC servo-loop that subtracts current from the input signal, a coarse servo-loop and a fine servo-loop can be used. The coarse servo-loop has discrete output levels where as the fine servo-loop has a continuous output range. Therefore, the output range of the fine servo-loop in the prior implementation can be reduced while the coarse-fine servo-loop is still capable of supplying the same output range.

However, the implementation of the coarse amplifier is critical such that the time constant of the output of the coarse servo-loop must be much slower than the $(1/2\pi f_{HP})$, where $f_{HP}$ is the high-pass filter cut-off frequency of the instrumentation amplifier that is defined by the fine servo-loop. In this case, the effect of the changing coarse servo-loop to the output of the instrumentation amplifier can be minimized by the fine servo-loop. Therefore, the crucial need is to implement a large-time constant inside the coarse servo-loop so that the output of the coarse servo-loop changes very slowly, when it updates its output.

Figure 1A:
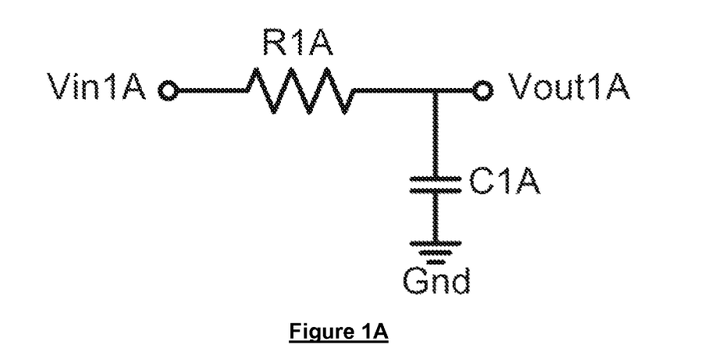
FIGS. 1A-1C show examples of the realization of a large time constant in the prior art.
Figure 1B:
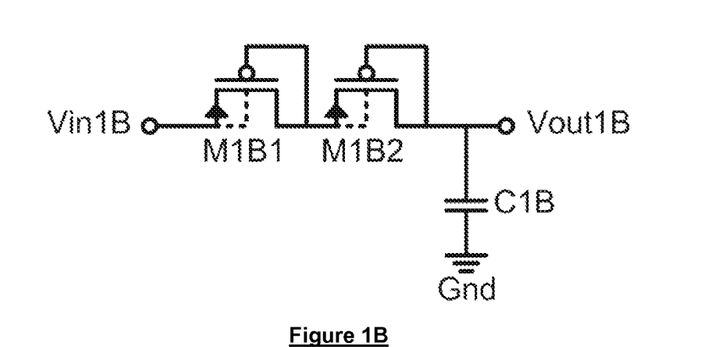
Figure 1C:
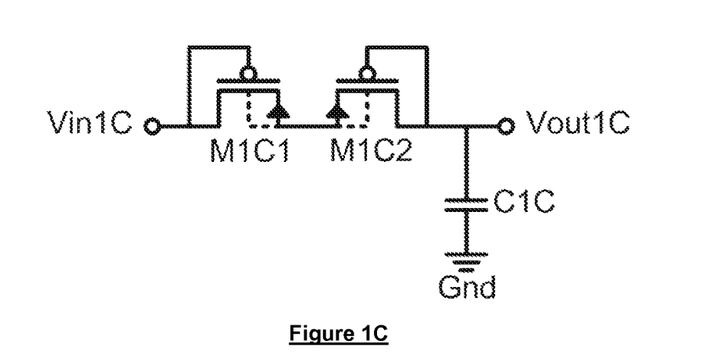

Large time constant implementations are presented in FIG. 1A, FIG. 1B and FIG. 1C. FIG. 1A uses an on-chip resistor, R1A, connected between the input, Vin1A, and the output, Vout1A, and an on-chip capacitor, C1A, connected between the output and the ground. However, considering the necessity for a high-pass filter cut-off frequency in the range of 0.1 Hz to 1 Hz for most of the biomedical signal acquisition systems, the time constant of this architecture must be set much lower than $1/(2\pi(0.1 \text{ Hz}))$, which leads to extremely large silicon area if implemented using architecture of FIG. 1A.

FIG. 1B shows the realization of a large time constant where the resistors are implemented by using pseudo resistors [3]. FIG. 1C shows the realization of a large time constant where the resistors are implemented using the structure proposed in [4]. Both approaches can occupy very small area, however, they suffer from the fact that the input voltage swing is only limited to less than hundred millivolts. This is due to the fact that the PMOS transistors of FIG. 1B and FIG. 1C operate in weak inversion, and a large input signal will increase the source-to-gate voltage of the PMOS transistors. This further turns on the transistor, leading to reduced time constant. Therefore, both the implementation of FIG. 1B and FIG. 1C needs the series connection of large number of transistors in order to improve their input range. This can lead to large silicon area consumption.

SUMMARY

According to the first aspect of the invention, a large time constant steering circuit is proposed for slowly changing a voltage on a node between at least two discrete voltage levels. The circuit comprises an input node for receiving an input voltage, an output node for presenting an output voltage, a capacitive part connected at said output node for providing said output voltage and a resistive part connected between said input and output nodes for conducting a charging current from said input node to said capacitive part or a discharging current from said capacitive part to said input node depending on said input voltage. The resistive part comprises a semiconductor structure connectable between said input node and said capacitive part in such a way that the semiconductor structure remains in a substantially non-conducting state (i.e. an OFF state) irrespective of the input and output voltages and passes only leakage currents for charging or discharging said capacitive part. So the capacitive part is charged and discharged by leakage currents only.

In preferred embodiments, the circuit is formed by two PMOS transistors and a capacitor. This circuit uses only passive components, occupies minimal area, has a wide input swing and does not consume any static power. The substrates of the PMOS transistors are preferably connected together, which are also connected to the sources of the PMOS transistors. The gates of the PMOS transistors can be tied to the supply voltage to prevent switching ON. Hence, the PMOS transistors can operate in their OFF state independent of the input voltage level. This is in contrast to implementations where the transistors are operating in weak inversion like in the prior art. Therefore, the circuit of this embodiment of the present invention will have a large time constant that is independent from the input voltage swing, whereas the other implementations are very sensitive to the input voltage swing.

In embodiments according to the invention, the large time constant steering circuit is used to implement an intentionally slow steering current digital-to-analog converter (DAC), which may in turn be used to implement a coarse servo-loop of an instrumentation amplifier with high-pass filter characteristics, in particular an AC coupled chopper stabilized instrumentation amplifier (ACCIA). The fine servo-loop of the ACCIA is preferably implemented by a transconductance stage.

BRIEF DESCRIPTION OF THE DRAWINGS

Presently preferred embodiments are described below in conjunction with the appended drawing figures, wherein like reference numerals refer to like elements in the various figures, and wherein.

DETAILED DESCRIPTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

The present invention includes a circuit that realizes a large time constant, which uses only passive components. The circuit occupies minimal area and does not consume any static power. In addition to that, the time constant of the circuit is minimally dependent on the input voltage swing.

Figure 2:
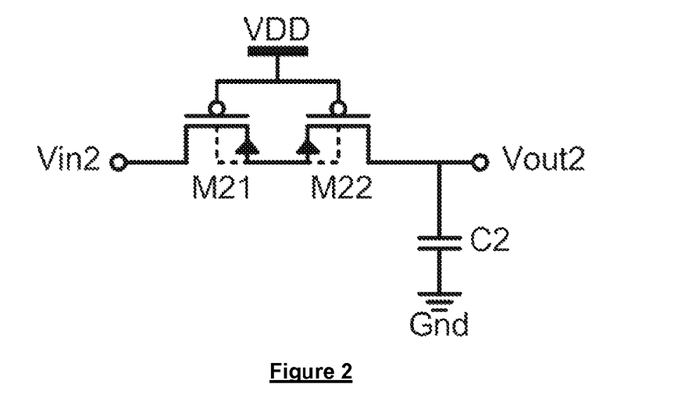
FIG. 2 shows a preferred embodiment of a large time constant steering circuit according to the invention.

A preferred embodiment of the circuit is illustrated in FIG. 2. The circuit comprises two PMOS transistors, M21 and M22, and a load capacitor, C2. The substrates of the PMOS transistors are connected together, which are also connected to the sources of the PMOS transistors. The gates of the PMOS transistors are tied to the supply voltage. Hence, the PMOS transistors are always operating in their OFF state independent of the input voltage level. This is in contrast to the implementations in FIG. 1B and FIG. 1C, where the transistors are operating in weak inversion. As it will be further explained later on, this is the main reason for the circuit of the present invention to have a large time constant that is independent from the input voltage swing, whereas the other implementations of FIG. 1B and FIG. 1C are very sensitive to the input voltage swing. Note that the implementation assumes that the available technology is an n-well or a twin-well process. The same architecture can be implemented using NMOS transistors in a p-well or a twin-well process.

Figure 3:
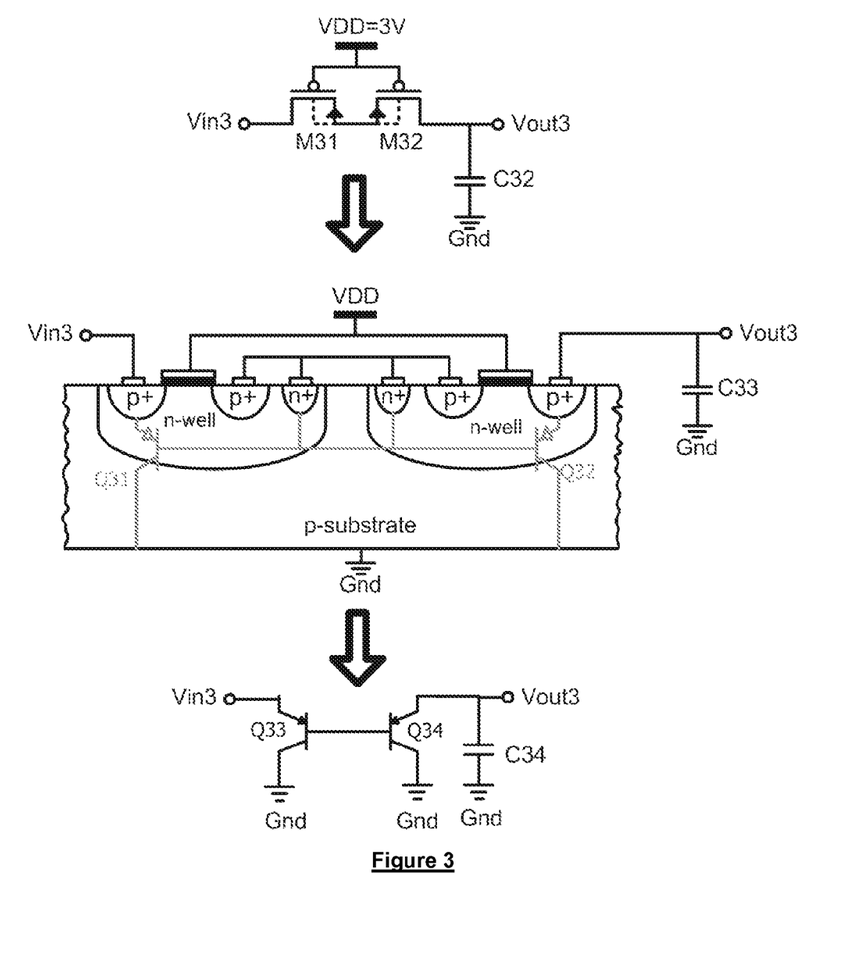
FIG. 3 illustrates the equivalent circuit of the circuit of FIG. 2.

A more detailed description of the circuit of FIG. 2 is given by FIG. 3. A parasitic PNP bipolar transistor is created for each of the PMOS transistors by the drain, the n-well and the p-substrate of this PMOS transistor. Since the PMOS transistors are in OFF state, the only available path for the current to flow is through the parasitic PNP bipolar transistors, Q31 and Q32. Due to the fact that the source and the bulk connections of the PMOS transistors M31 and M32 are shorted, the bases of the parasitic PNP bipolar transistors Q31 and Q32 are also shorted. As a result, the two MOS transistors are equivalent to two base-to-base connected PNP bipolar transistors.

Figure 4:
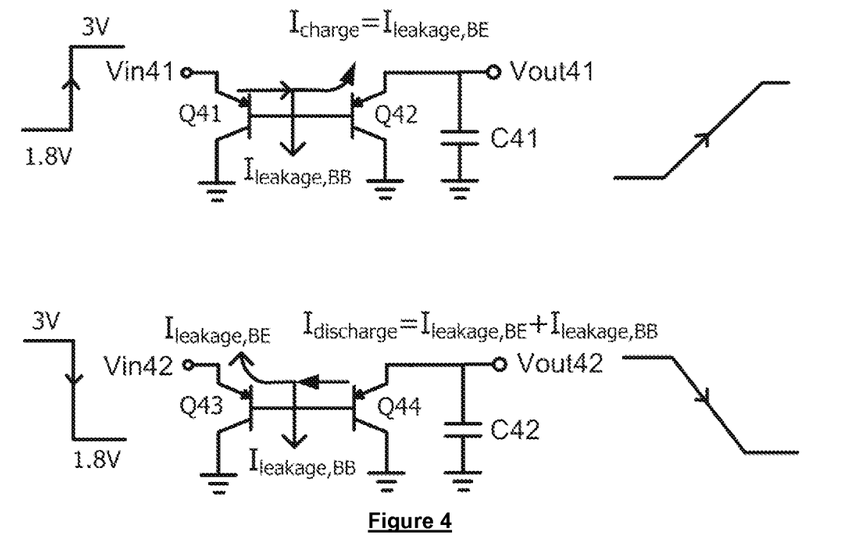
FIG. 4 describes the mechanisms that charge and discharge the load capacitance of the circuit of FIG. 2.

FIG. 4 describes the flow of current when a step voltage input is applied to the circuit that implements large time constant. For the clarity of the drawing, only the equivalent model of the implementation is presented, which is two base-to-base connected PNP bipolar transistors.

Assuming that a step input with a rising edge is applied to the circuit, the base-emitter diode of the PNP bipolar transistor Q41 is forward biased. This reduces the resistance between the input node and the common base of the PNP bipolar transistors Q41 and Q42. On the other hand, the base-emitter diode of the PNP bipolar transistor Q42 is reverse biased. Therefore, the only current that can charge the load capacitor C41 is the leakage current of the reverse biased base-emitter diode of the PNP bipolar transistor Q42. This charging continues till the voltage at Vout41 equals to the voltage of the common base of the bipolar transistors Q41 and Q42. This voltage is slightly lower than the input voltage due to the leakage current $I_{leakage,BB}$, which is the leakage current of the reverse biased diode between the common base and the p-substrate.

Assuming that a step input with a falling edge is applied to the circuit that implements the large time constant, the two different leakage currents discharge the common base of the PNP bipolar transistors. The first leakage current is due to the reverse biased base-emitter diode of Q43, $I_{leakage,BE}$, and the second current is the leakage current of the reverse biased diode between the common base of the PNP bipolar transistors and the p-substrate, $I_{leakage,BB}$. Once the voltage level at the common base starts to decrease, the base-emitter diode of the PNP bipolar transistor, Q44, conducts. Thus, the voltage at Vout42 follows the voltage at the common base of the PNP bipolar transistors Q43 and Q44. Therefore, the load capacitance C42 is discharged by a total current of $I_{leakage,BE} + I_{leakage,BB}$.

As a result, the charging and discharging currents of the load capacitor can be given as:

$$\frac{\partial V_{C_L}}{\partial t} = \begin{cases} I_{leakage,BE}/C_L \Leftrightarrow \text{input} \uparrow \\ (I_{leakage,BE} + I_{leakage,BB})/C_L \Leftrightarrow \text{input} \downarrow \end{cases} \quad (1)$$

Due to that fact that the reverse bias leakage currents of both the base-emitter diode and common-base to p-substrate diode are very small, the time constant of the output voltage is very large. In addition, the reverse bias leakage has minor dependence on the reverse bias voltage, so the time constant of the implementation has minor dependence on the input voltage swing.

Figure 5:
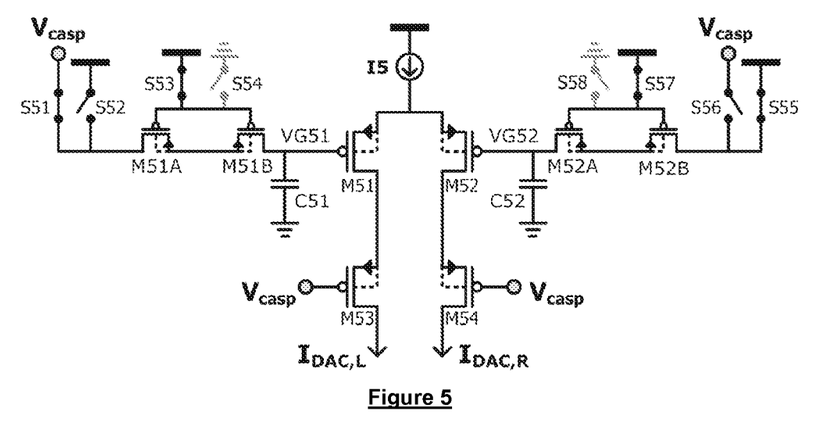
FIG. 5 shows the implementation of an intentionally slow steering DAC according to the invention.

The present invention enables the implementation of a slow steering DAC that can be used in the coarse servo-loop of the ACCIA, but this invention is not limited thereto. FIG. 5 shows the implementation of the slow steering current DAC. The realization consists of a current source, I5, two pass gates M51 and M52, and two cascade transistors, M53 and M54. The purpose of the cascade transistors is to increase the output impedance of the current DAC and to make DAC current independent of the output voltage. The two pass gates control the current passing through the each branch of the current DAC, namely, $I_{DAC,L}$ and $I_{DAC,R}$, so that the tail current, I5, of the current DAC can be steered between the two branches.

The voltages of the pass gates are each controlled by a large time constant steering circuit as described above. As a result, the steering time of the current DAC is defined by the large time constant implementations that involve the components M51A, M51B and C51 for the left branch of the current DAC, and the components M52A, M52B and C52 for the right branch of the current DAC. The switches S51, S52, S55, and S56 control the input voltage to the large time constant implementations. The switches S53, S54, S57 and S58 control the gate voltages of the PMOS transistors M51A, M51B, M52A, and M52B. If the gates of the transistors M51A, M51B, M52A, and M52B are connected to the supply voltage, then these transistors and the load capacitors C51 and C52 implements two large time constant circuits. If the gates of the transistors M51A, M51B, M52A, and M52B are connected to the ground, then the transistors turn ON and fast steering of the current DAC can be realized.

Figure 6:
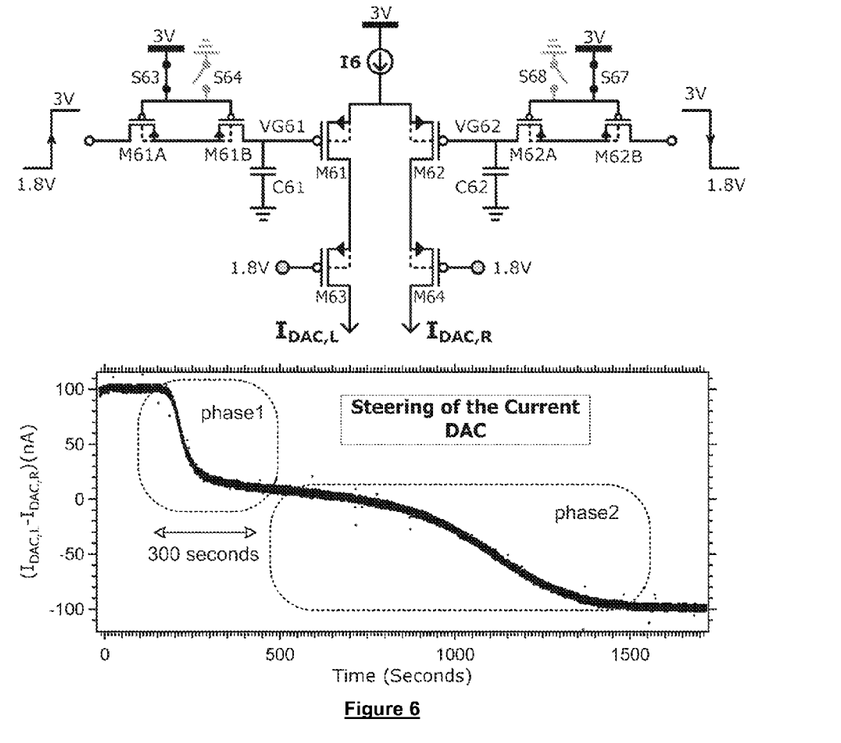
FIG. 6 illustrates the measurement from a slow steering DAC according to FIG. 5.

FIG. 6 demonstrates the operation of the slow steering current DAC by measuring the output current difference between the left and the right branches, $(I_{DAC,L}-I_{DAC,R})$. A step input with a rising edge from 1.8V to 3V is applied to the left input of the current DAC, and a step input with a falling edge from 3V to 1.8V is applied to the right input, simultaneously. Therefore, it should expected that the output current should steer from left to right, which equals to a decrease in $(I_{DAC,L}-I_{DAC,R})$. The gates of the transistors M61A, M61B, M62A, and M62B are connected to the supply voltage. Therefore, these transistors are turned OFF. As a result, the voltage at nodes VG61 and VG62 are controlled by the claimed large time constant implementation. The discharging current of the large time constant implementation is larger than the charging current, see Eq. (1). This indicates that the first phase of the DAC steering occurs mainly due to the discharge of capacitance C62 and the second phase occurs due to the charging of the capacitance C61. The total steering time is more than 1000 seconds when selecting C61 and C62 as 0.5 pF, and the fastest part of the steering occurs in slower than 300 seconds. This proves the operation of the claimed large time constant implementation even under large input voltage swing as much as 1.2V.

Figure 7:
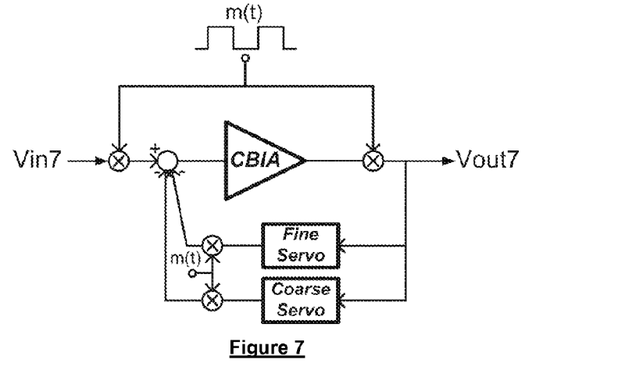
FIG. 7 illustrates the conceptual implementation of an AC coupled chopper stabilized instrumentation amplifier (ACCIA) according to a preferred embodiment of the invention.

FIG. 7 illustrates the conceptual implementation of an ACCIA according to the invention. The high-pass filter characteristic is introduced to the ACCIA by utilizing a coarse servo-loop and a fine servo-loop. The fine servo-loop sets the cut-off frequency of the high-pass filter characteristics and supplies a continuous analog output. On the other hand, the coarse servo-loop has discrete output steps, where each step corresponds to the half of the output range of the fine servo-loop. Therefore, once the output of the fine servo-loop reaches its limit, the coarse DC servo-loop updates its output that sets the output of the fine servo-loop to its mid-range.

Figure 8:
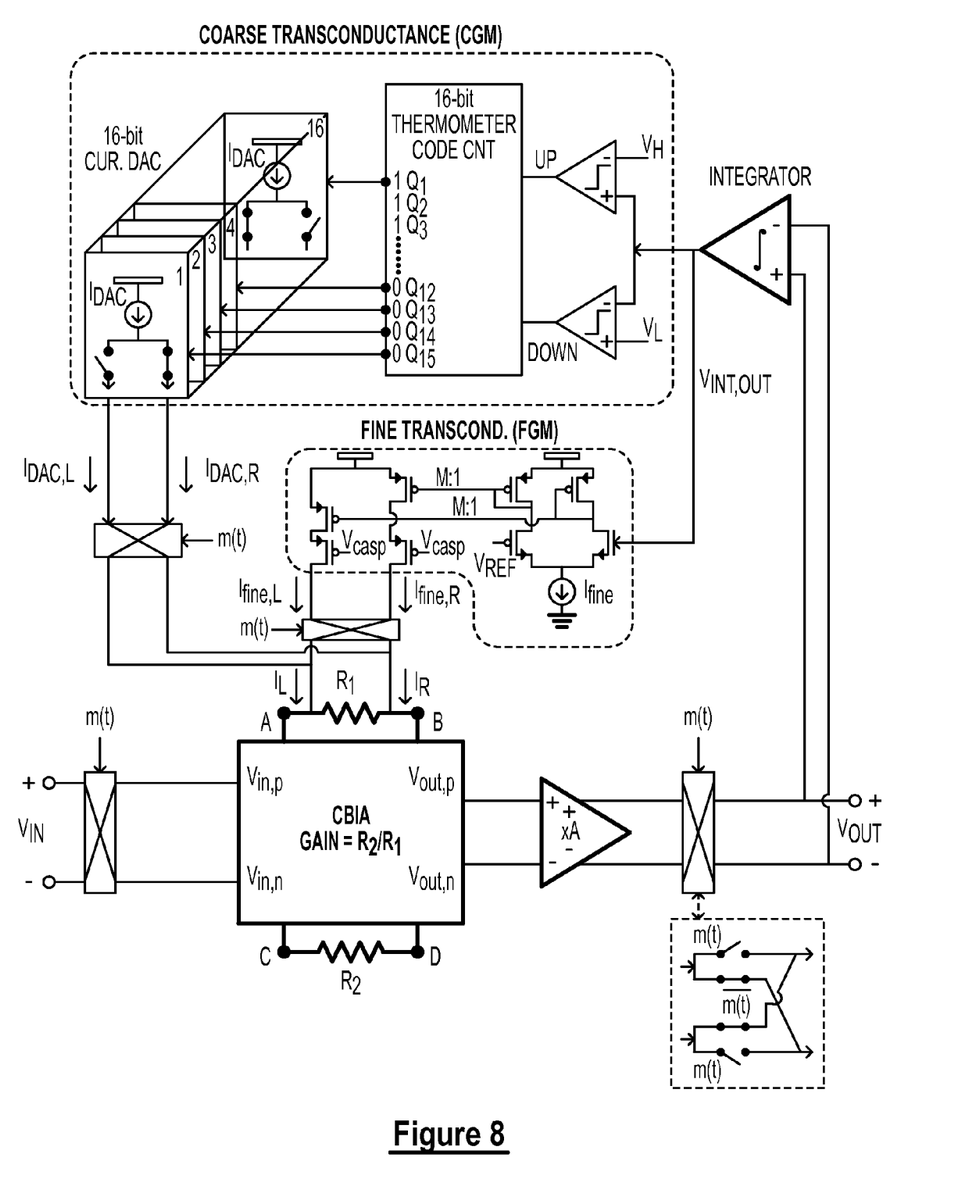
FIG. 8 illustrates a complete implementation of an ACCIA according to a preferred embodiment of the invention.

FIG. 8 illustrates the complete implementation of the ACCIA that utilizes the fine and coarse servo-loops for implementing high-pass filter characteristics. The core amplifier is a current balancing instrumentation amplifier (CBIA). The operation of the core amplifier can be described as follows: the input voltage is copied to the terminals of $R_1$. This voltage creates a current through $R_1$ that is supplied by the ACCIA. This current is sensed by the CBIA and the same current is supplied to $R_2$. The current through $R_2$ creates the output voltage of the CBIA. Therefore, the gain of the CBIA is defined by the ratio of two resistors as $R_2/R_1$.

A second gain stage with high-pass filter characteristics further amplifies the output of the CBIA and filters the offset voltage of the CBIA. The fine servo-loop and the coarse servo-loop are connected to the output of an on-chip integrator. The purpose of the on-chip integrator is to sense the output DC level of the amplifier.

The fine servo-loop is implemented by a transconductance stage. If a DC input voltage is applied to the ACCIA, it is copied to the terminals of $R_1$. Under steady state, the current through $R_1$ due to the DC input is supplied by the fine servo-loop. Since, the CBIA does not supply the current through $R_1$, no current is copied to $R_2$. This means that the DC input to the instrumentation amplifier is not amplified.

If this DC voltage input to the ACCIA is out of the range of the maximum current that can be supplied by the fine servo-loop, then the coarse DC servo-loop sense this and updates its output in such a way that the DC servo-loop can supply enough current to filter the input DC voltage to the instrumentation amplifier.

More specifically, the fine transconductance stage can only supply enough current to filter an input DC voltage of:

$$V_{filter,fine} = \frac{|I_{fine,L} - I_{fine,R}|}{2} \times R_1 = \pm \frac{I_{fine} \times M}{2} R_1 \quad (2)$$

where M is the current mirror ratio of the fine transconductance stage. On the other hand, the coarse servo-loop is implemented by using the slow steering DAC implementation of FIG. 5. The combination of 16 slow steering current DACs creates a 16-bit slow steering current DAC. Each bit of this current DAC is controlled by a thermometer code counter. Two comparators check weather the fine transconductance stage has reached its limit. For instance lets assume that, the input DC voltage to the instrumentation amplifier is larger than the limit of the fine transconductance stage and the fine transconductance has reached the limit specified by Equation (2) and $I_{fine,L}-I_{fine,R}=+2\times I_{fine}$, where $I_{fine}$ is the tail current of the fine transconductance stage, and M equals to 2. Then the comparators of the coarse transconductance stage sense this and changes a bit of the 16-bit slow steering current DAC to increase $I_{DAC,L}$ and reduce $I_{DAC,R}$. The tail current of each DAC bit is set to $I_{fine}$. As the steering of the DAC starts, $I_{fine,L}-I_{fine,R}$ decreases from $+2\times I_{fine}$, and after the completion of the DAC steering, $I_{fine,L}-I_{fine,R}$ is set to zero. Therefore, the coarse-fine combination of the transconductance stage can filter an input DC voltage of:

$$\left[\left(\frac{I_{fine} \times M}{2}\right) + m_{DAC} \times I_{DAC}\right] \times R_1 \quad (3)$$

where $m_{DAC}$ is the number of DAC bits and $I_{DAC}$ is the tail current source of each DAC bit.

After this example, the importance of the slow steering DAC should become clear. Unless the steering of the DAC is not much slower than the $(1/2\pi f_{HP})$, where $f_{HP}$ is set by the integrator stage and the fine transconductance stage, and it must be in the rage of 0.1 Hz-1 Hz for most of the biomedical signal acquisition applications, then the steering of the DAC would create a voltage step at the output of the instrumentation amplifier. This is undesired since it can saturate the output of the instrumentation amplifier.

The $f_{HP}$ is defined by:

$$f_{HP} = [g_{m,fine} \cdot M \cdot A_{v,INT}] \times [R_2 \cdot A] \times f_{LP,INT} \quad (4)$$

where $g_{m,fine}$ is the transconductance of the input pair stage of the fine transconductance stage, M is the mirror ratio of the fine transconductance stage, $A_{v,INT}$ is the open loop gain of the on-chip integrator, A is the gain of the second gain stage connected to the output of the CBIA, and $f_{LP,INT}$ is the low-pass corner frequency of the on-chip integrator. The result of this equation for the current implementation is 0.1 Hz. Since even the fastest steering time of the slow steering DAC is 300 seconds, which is much slower that $(1/2\pi f_{HP})$, the fine transconductance stage can prevent the step response at the output.

The main advantage of using such fine-coarse architecture is the reduction of the current that is consumed in the fine transconductance stage. It should be noted that the current consumed in the input stage of the fine transconductance stage is wasted. On the other hand, the 16-bit slow steering current DAC actually supplies the bias current of the CBIA, therefore the increase in the DAC current also reduces the noise of the CBIA. If the figure of merit is defined by the following equation:

$$FOM \cong K \times V_{rms,in} \times \sqrt{\frac{I_{total}}{BW}} \quad (5)$$

where K is a constant, $V_{rms,in}$ is the input referred noise of the ACCIA, $I_{total}$ is the total current consumption of the ACCIA, and BW is the noise bandwidth of the ACCIA, then the difference between using only the fine transconductance stage and using the fine-coarse transconductance stages for the same input DC filtering limit is nearly a factor of two.

In a preferred embodiment, this ACCIA is used as a front-end of a readout channel. The proposed circuit can for example be used in an EEG acquisition system. A complete EEG Acquisition ASIC can be designed (see FIG. 9), where the outputs of the analog readout front-ends can be digitized using the on-chip low-power ADC. This eliminates the use of an external ADC that not only improves the power dissipation of the EEG acquisition system but also can shrink the system size.

Figure 9:
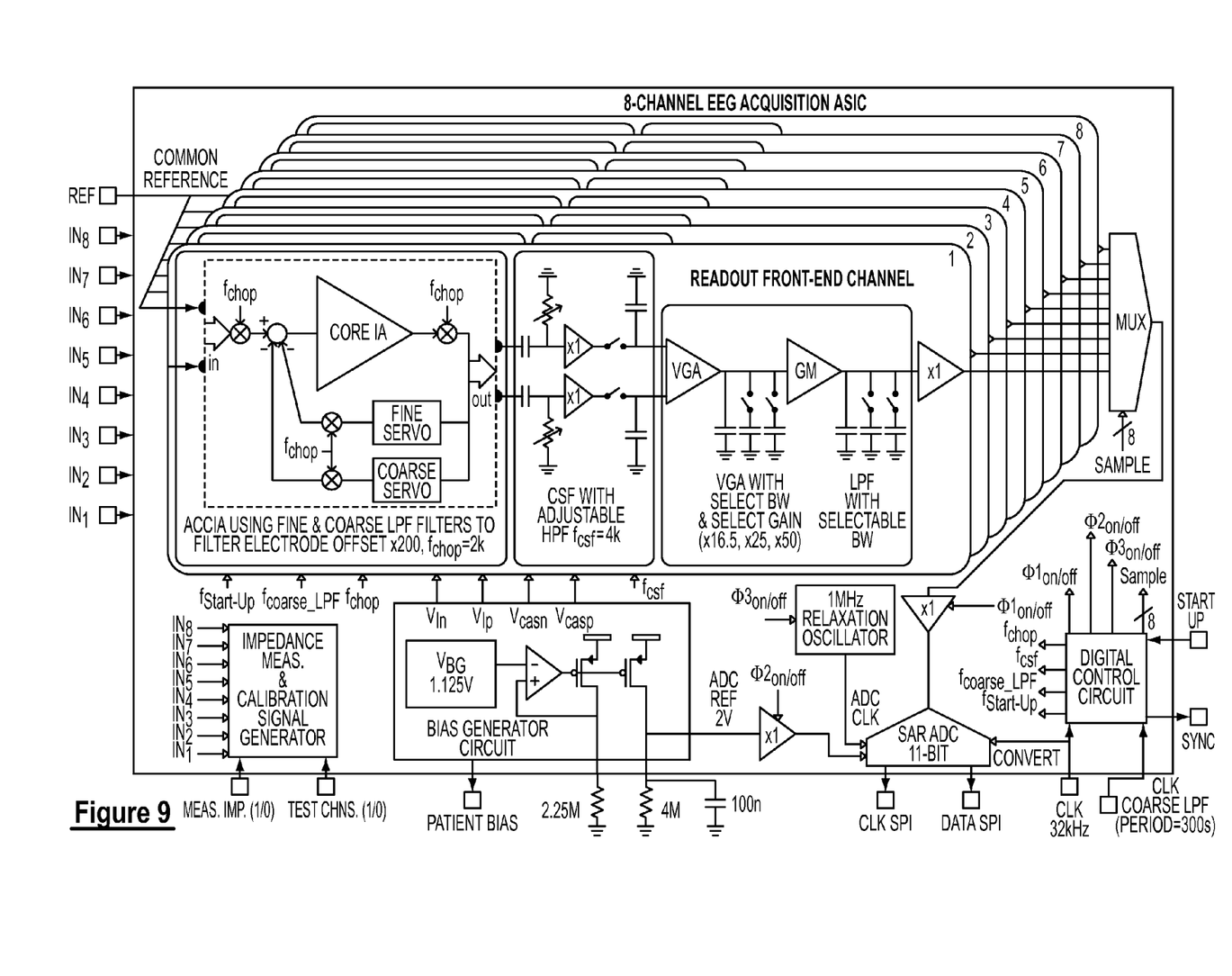
FIG. 9 illustrates an 8-channel EEG acquisition ASIC according to a preferred embodiment of the invention.

FIG. 9 shows the architecture of the proposed EEG acquisition ASIC. The main building blocks of the ASIC are: eight readout front-end channels, an 11-bit SAR ADC, a bias circuit, a 1 MHz relaxation oscillator, an electrode impedance measurement circuit, and a calibration signal generator. The readout front-end channels are responsible for extracting and conditioning the EEG signals from the biopotential electrodes. The preamplifier of a readout channel is the presented ACCIA. The ACCIA is followed by a chopping spike filter (CSF) stage, which includes a HPF with adjustable cut-off frequency. After the CSF stage a programmable gain stage further amplifies the extracted biopotential signals. The output of each channel is buffered and time-multiplexed. Finally, a class-AB buffer buffers the outputs of the channels and drives the input capacitance of the ADC.

The ADC of the ASIC is implemented using the SAR-ADC architecture due to its low-power dissipation characteristics. The operating clock of the ADC is generated by the on-chip 1 MHz relaxation oscillator. The operation of the relaxation oscillator is duty cycled such that it generates the 1 MHz clock only when the ADC is asked to convert an analog input signal. The reference voltage of the ADC is generated by the bias circuit, and it is buffered by a class-AB buffer to drive the capacitive DAC of the SAR-ADC.

The ASIC is designed for battery powered systems, where the supply voltage changes as the battery discharges. Therefore, the bias generator circuit of the ASIC uses a PTAT voltage generator to generate a temperature and supply independent reference voltage. This reference voltage is used to generate all the bias voltages and currents of the ASIC, as well as the reference voltage of the ADC. Additionally, it should be noted that the patient bias voltage that is used for the grounding of the patient is also generated by the bias generator circuit.

The digital control circuit of the ASIC uses a 32 kHz clock input from which the sample signals of the analog multiplexer is generated, and to which the operation of the ADC is synchronized. The sample time of the first channel of the ASIC can be used as a synchronization signal with an external microcontroller. Additionally, the digital control circuit accepts a clock signal with 1 ms pulse duration and 300 s period. This clock is necessary for the operation of the coarse transconductance stage of the ACCIA. During this 1 ms pulse time the coarse transconductance stage checks whether the fine transconductance stage has reached its limits. If so, the coarse transconductance stage adjusts its output accordingly. However, this slow operation of the coarse transconductance stage can make the start-up of the ACCIA circuit extremely slow. Therefore, the ASIC has a start-up mode.

Finally, the ASIC includes an electrode impedance measurement and calibration modes, which enable the user to measure the impedances of the biopotential electrodes and to calibrate the matching of the readout front-end channels, respectively.

References, which are Hereby Incorporated in its Entirety

[1] R. F. Yazicioglu, P. Merken, R. Puers, and C. Van Hoof, "60 µW 60 nV/pHz readout front-end for portable biopotential acquisition systems," IEEE J. Solid-State Circuits, vol. 42, no. 5, pp. 1100-1110, May 2007.

[2] T. Denison, K. Consoer, W. Santa, T. Avestruz, J. Cooley, and A. Kelly, "a 2 µW 100 nV/√Hz Chopper-Stabilized Instrumentation Amplifier for Chronic Measurement of Neural Field Potentials," IEEE J. Solid-State Circuits, vol. 42, no. 12, December 2007.

[3] R. R. Harrison and C. Cameron, "A Low-Power Low-Noise CMOS Amplifier for Neural Recording Applications," IEEE J. Solid-State Circuits, vol. 38, no. 6, June 2003.

[4] R. H. Olsson, M. N. Gulari, and K. D. Wise, "A Fully-Integrated Bandpass Amplifier for Extracellular Neural Recording," IEEE EMBS Conf. on Neural Eng., Italy, March 2003.

The invention claimed is:

1. An instrumentation amplifier device comprising:
a current balancing instrumentation amplifier for amplifying an input signal to an amplified output signal; and
a DC servo-loop for removing a DC-component from the input signal,
wherein the DC servo-loop includes a coarse servo-loop providing discrete output levels and a fine servo-loop providing a substantially continuous output level in a range between a first limit and a second limit, the coarse servo-loop having a large time constant for slowly changing to one of the discrete output levels upon the fine servo-loop reaching one of the first limit and the second limit.

2. The instrumentation amplifier device according to claim 1, wherein a difference between any two adjacent discrete output levels of the coarse servo-loop is smaller than the range.

3. The instrumentation amplifier device according to claim 1, wherein a difference between any two adjacent discrete output levels of the coarse servo-loop is half the range of the fine servo-loop.

4. The instrumentation amplifier device according to claim 1, wherein the coarse servo-loop comprises at least one large time constant steering circuit for slowly changing between two of its discrete output levels.

5. The instrumentation amplifier device according to claim 1, wherein the coarse servo-loop comprises at least one slow steering current digital to analog converter (DAC) for slowly changing between two of the discrete output levels.

6. The instrumentation amplifier device according to claim 1, wherein the fine servo-loop comprises a transconductance stage.

7. An electroencephalogram (EEG) acquisition application-specific integrated circuit (ASIC) comprising at least one instrumentation amplifier device according to claim 1.

* * * * *